(12) United States Patent
Fukuoka

(10) Patent No.: US 9,804,339 B2
(45) Date of Patent: Oct. 31, 2017

(54) OPTICAL CONNECTOR AND MEDICAL DEVICE

(71) Applicant: Sony Olympus Medical Solutions Inc., Tokyo (JP)

(72) Inventor: Morinao Fukuoka, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 108 days.

(21) Appl. No.: 14/732,055

(22) Filed: Jun. 5, 2015

(65) Prior Publication Data

US 2015/0374207 A1   Dec. 31, 2015

(30) Foreign Application Priority Data

Jun. 27, 2014 (JP) ................. 2014-133332

(51) Int. Cl.
*G02B 6/38* (2006.01)
*G02B 23/24* (2006.01)
*A61B 1/00* (2006.01)
*G02B 1/115* (2015.01)

(52) U.S. Cl.
CPC ........ *G02B 6/3818* (2013.01); *A61B 1/00013* (2013.01); *A61B 1/00126* (2013.01); *G02B 1/115* (2013.01); *G02B 23/2446* (2013.01); *G02B 23/2492* (2013.01)

(58) Field of Classification Search
CPC .. G02B 6/3818; G02B 23/2446; G02B 1/115; G02B 23/2492; A61B 1/00013; A61B 1/00126
See application file for complete search history.

(56) References Cited

U.S. PATENT DOCUMENTS

| 6,852,455 B1 * | 2/2005 | Lyons ................... G03F 1/54 430/5 |
| 7,181,106 B2 * | 2/2007 | Ushiro ................. G02B 5/1857 359/566 |

FOREIGN PATENT DOCUMENTS

| JP | 5-176884 A | 7/1993 |
| JP | 2011-10886 A | 1/2011 |

* cited by examiner

*Primary Examiner* — Ryan Lepisto
(74) *Attorney, Agent, or Firm* — Oblon, McClelland, Maier & Neustadt, L.L.P.

(57) ABSTRACT

An optical connector for coupling to a counter-connector mechanically and optically, a portion of an optical transmission line transmitting an optical signal being disposed in the optical connector, includes: a first outer case through which the optical transmission line is inserted and that covers an incidence end or an emitting end of an optical signal through the optical transmission line; a cover plate that is permeable to an optical signal and seals a tip end side coupled to the counter-connector in the first outer case; and a coating film made of amorphous carbon that is disposed on a surface on the tip end side of the cover plate.

14 Claims, 6 Drawing Sheets

OPTICAL CONNECTOR AND MEDICAL DEVICE

CROSS-REFERENCE TO RELATED APPLICATIONS

The present application claims priority to and incorporates by reference the entire contents of Japanese Patent Application No. 2014-133332 filed in Japan on Jun. 27, 2014.

BACKGROUND OF THE INVENTION

1. Field of the Invention

The present invention relates to an optical connector and a medical device.

2. Description of the Related Art

Imaging technologies have been developed that are accompanied with high-quality image data of a 4K image, for example. In response to such development of imaging technologies, also in the medical field, a medical device that is capable of observing a subject using high-quality image data is desired to become widespread. For observing a subject in real-time using high-quality image data, transmitting a large amount of image data at a high speed is necessary. Conventionally, a metal cable has been used for medical devices, which has a limited transmission capacity and a limited transmission rate. This makes it difficult to achieve the observation of a subject in real-time using high-quality image data with a metal cable.

In view of the conventional circumstances described above, data transmission technologies using optical signals have been disclosed for transmitting a large amount of image data at a high speed in medical devices (refer to Japanese Laid-open Patent Publication No. 05-176884 and Japanese Laid-open Patent Publication No. 2011-10886). In such a transmission technology, data is transmitted through an optical connector for achieving mechanical and optical connection in the middle of a transmission line.

The configuration of a typical optical connector includes a portion of an optical fiber that transmits an optical signal disposed in a cylindrical outer case. The optical connector is mechanically coupled to a counter optical connector. This coupling enables the incidence end of an optical signal through one optical fiber to face the emitting end of an optical signal through the other optical fiber and vice versa. Alternatively, this coupling enables the emitting end of an optical signal through one optical fiber to face the incidence end of an optical signal through the other optical fiber and vice versa. In this manner, optical signals can be transmitted between the optical fibers.

In medical devices such as an endoscope apparatus, sterilization is usually performed using an autoclave before examining a subject. This is performed to prevent the subject from being infected with pathogenic bacteria and the like. It is not understood, however, which material is resistant to an autoclave and thus favorable for the above-described transmission of optical signals.

There is a need for an optical connector and a medical device that have resistance to an autoclave and are suitable for transmitting an optical signal.

SUMMARY OF THE INVENTION

It is an object of the present invention to at least partially solve the problems in the conventional technology.

According to one aspect of the present invention, there is provided an optical connector for coupling to a counter-connector mechanically and optically, a portion of an optical transmission line transmitting an optical signal being disposed in the optical connector, the optical connector including: a first outer case through which the optical transmission line is inserted and that covers an incidence end or an emitting end of an optical signal through the optical transmission line; a cover plate that is permeable to an optical signal and seals a tip end side coupled to the counter-connector in the first outer case; and a coating film made of amorphous carbon that is disposed on a surface on the tip end side of the cover plate.

According to another aspect of the present invention, there is provided a medical device capturing an image of a subject. The medical device includes: an optical connector for coupling to a counter-connector mechanically and optically, a portion of an optical transmission line transmitting an optical signal being disposed in the optical connector, the optical connector including: a first outer case through which the optical transmission line is inserted and that covers an incidence end or an emitting end of an optical signal through the optical transmission line; a cover plate that is permeable to an optical signal and seals a tip end side coupled to the counter-connector in the first outer case; and a coating film made of amorphous carbon that is disposed on a surface on the tip end side of the cover plate.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
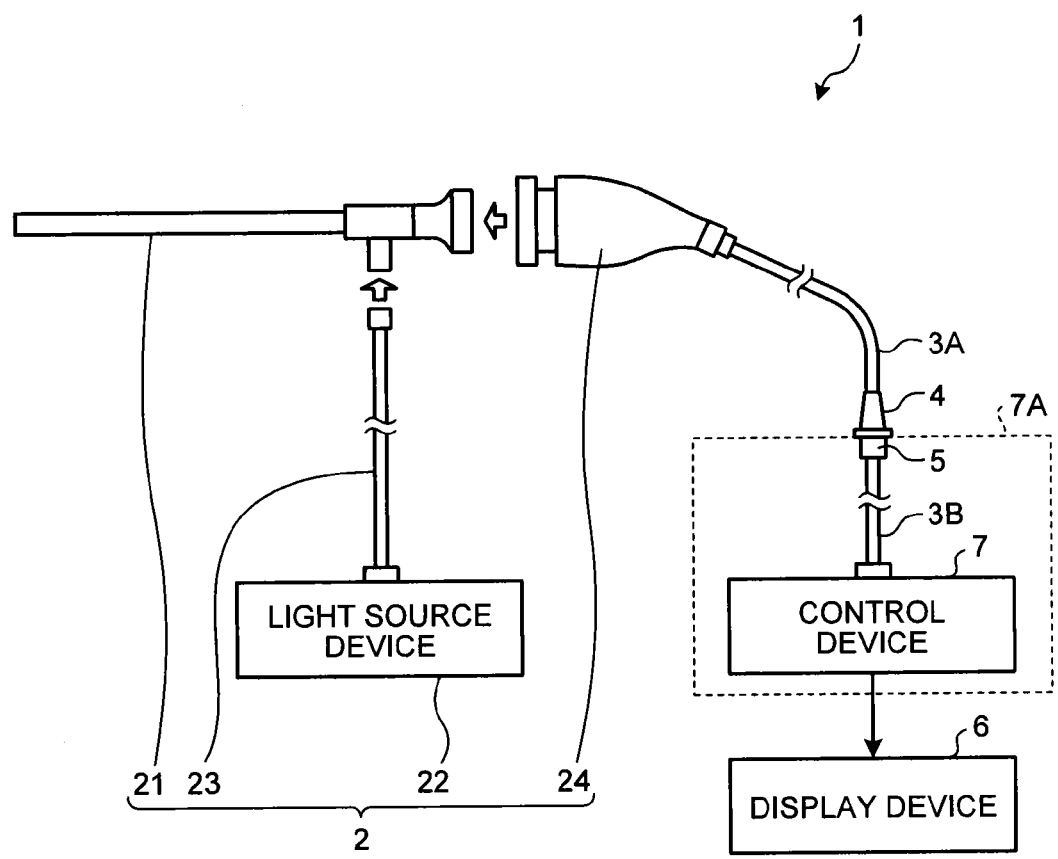
FIG. 1 is a view illustrating an outline configuration of an endoscope apparatus according to an embodiment of the present invention.

Preferred Embodiments of the Present Invention (hereinafter referred to as the embodiment) will be explained with reference to accompanying drawings. The present invention, however, is not limited to the following embodiments. The components identical to each other are designated by the respective identical reference numerals in the drawings.

Outline Configuration of the Endoscope Apparatus

FIG. 1 is a view illustrating the outline configuration of an endoscope apparatus 1 according to the embodiment of the present invention.

The endoscope apparatus 1 is a device used in the medical field for observing the inside of an observation object such as a human body (inside of a living body). That is, the endoscope apparatus 1 corresponds to a medical device according to the embodiment of the present invention. The endoscope apparatus 1 includes, as illustrated in FIG. 1, an endoscope 2, first and second transmission cables 3A and 3B, a plug 4, a receptacle 5, a display device 6, and a control device 7.

In the description of the present embodiment, a rigid endoscope (an insertion unit 21 (FIG. 1)) serves as the endoscope 2 in the endoscope apparatus 1. The description is provided merely for exemplary purpose and not limiting. For another example, a flexible endoscope (not illustrated) may serve as the endoscope 2 in the endoscope apparatus 1. Also in the description of the present embodiment, the endoscope 2 includes a camera head 24 (FIG. 1) separated from the insertion unit 21. The description is provided merely for exemplary purpose and not limiting. For another example, the endoscope 2 may include the camera head 24 integrated with the insertion unit 21. The endoscope apparatus may include the endoscope 2 that is an ultrasonic endoscope having a probe for ultrasonography.

The endoscope 2 captures an image of a living body (inside of the subject) and outputs an imaging signal of the image. The endoscope 2 includes, as illustrated in FIG. 1, an insertion unit 21, a light source device 22, a light guide 23, and a camera head 24.

The insertion unit 21 has hardness and an elongated shape, and is inserted into the living body. The insertion unit 21 includes an optical system including one or more lenses and condenses an image of an object.

The light source device 22 is coupled to an end of the light guide 23 and supplies a light to the end of the light guide 23 for illuminating a living body.

The light guide 23 has an end detachably coupled to the light source device 22 and the other end detachably coupled to the insertion unit 21. The light guide 23 transmits a light supplied by the light source device 22 from its one end to the other end, and then supplies the light to the insertion unit 21. The light supplied to the insertion unit 21 is emitted from the tip end of the insertion unit 21 and irradiates the living body. The light irradiating the living body (an image of the object) is condensed by the optical system in the insertion unit 21.

The camera head 24 is detachably coupled to the base end of the insertion unit 21. The camera head 24 includes an imaging device (not illustrated) and a photoelectric conversion element (not illustrated). The imaging device captures an image of the object and outputs an imaging signal (an electric signal). The photoelectric conversion element photoelectrically converts the imaging signal output from the imaging device (the electric signal) into an optical signal. Subsequently, the camera head 24 captures an image of the object obtained by condensing the light through the insertion unit 21 under the control of the control device 7 and photoelectrically converts an imaging signal generated through the image-capturing (an electric signal) into an optical signal. The camera head 24 then outputs the optical signal.

The first transmission cable 3A is a composite cable including an optical fiber 3A1 (refer to FIG. 4) and a plurality of electric signal cables 3A2 (refer to FIG. 4) inside of the outer sheath (not illustrated) of the cable serving as the outermost layer. The optical fiber 3A1 is an optical transmission line that transmits an optical signal (the imaging signal) output from the camera head 24. One end of the first transmission cable 3A is coupled to the camera head 24.

Figure 4:
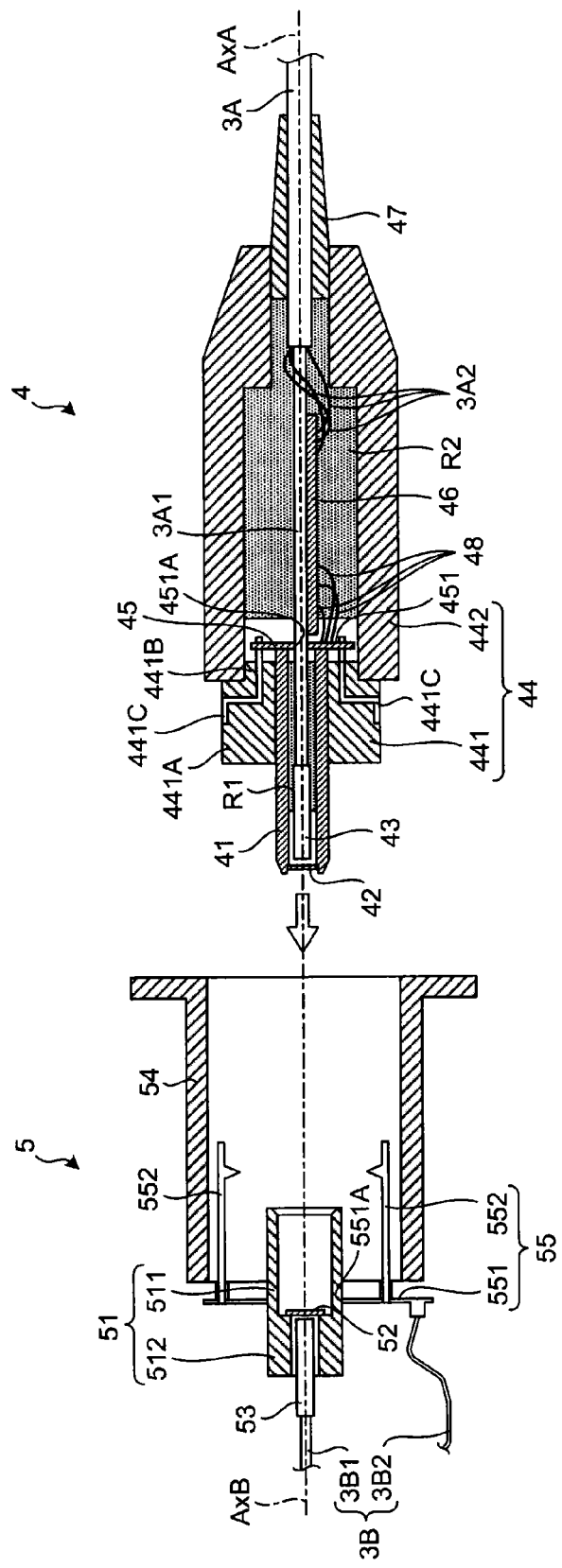
FIG. 4 is a cross-sectional view of the plug and the receptacle illustrated in FIG. 2 taken along the plane going through the central axis in the coupling direction of the plug and the receptacle.

The second transmission cable 3B is a composite cable including, in the same manner as the first transmission cable 3A, an optical fiber 3B1 (refer to FIGS. 2 and 4) and a plurality of electric signal cables 3B2 (refer to FIG. 4). One end of the second transmission cable 3B is coupled to the control device 7.

The plug 4 is a male connector corresponding to the optical connector according to the embodiment of the present invention. The plug 4 is coupled to the other end of the first transmission cable 3A.

The receptacle 5 is a female connector corresponding to the counter-connector. The receptacle 5 is coupled to the other end of the second transmission cable 3B.

The plug 4 and the receptacle 5 are coupled to each other, whereby the first and second transmission cables 3A and 3B are electrically and optically coupled to each other, thereby allowing transmission of electric signals and optical signals.

If the receptacle 5 is provided in or to a housing 7A (illustrated with a dashed line in FIG. 1) of the control device 7, the receptacle 5 is fixed to the housing 7A of the control device 7, whereby the receptacle 5 is readily detached from the plug 4. The receptacle 5 is not necessarily provided in or to the housing 7A of the control device 7, and may be provided outside of the housing 7A.

The configuration of the plug 4 and the receptacle 5 are described in detail later.

The display device 6 displays an image thereon under the control of the control device 7.

The control device 7 includes a central processing unit (CPU) and a graphics processing unit (GPU), and controls operations of the camera head 24 and the display device 6 totally.

Specifically, the control device 7 acquires an optical signal output through the first and second transmission cables 3A and 3B (optical fibers) from the camera head 24 (an imaging signal) and photoelectrically converts the optical signal into an electric signal. Subsequently, the control device 7 performs various types of image processes on the photoelectrically converted electric signal, thereby displaying an image captured by the camera head 24 on the display device 6. The control device 7 outputs a control signal and the like through the first and second transmission cables 3A and 3B (electric signal cables) to the camera head 24.

Configuration of the Plug and the Receptacle

The following describes the configuration of the plug 4 and the receptacle 5.

Figure 2:
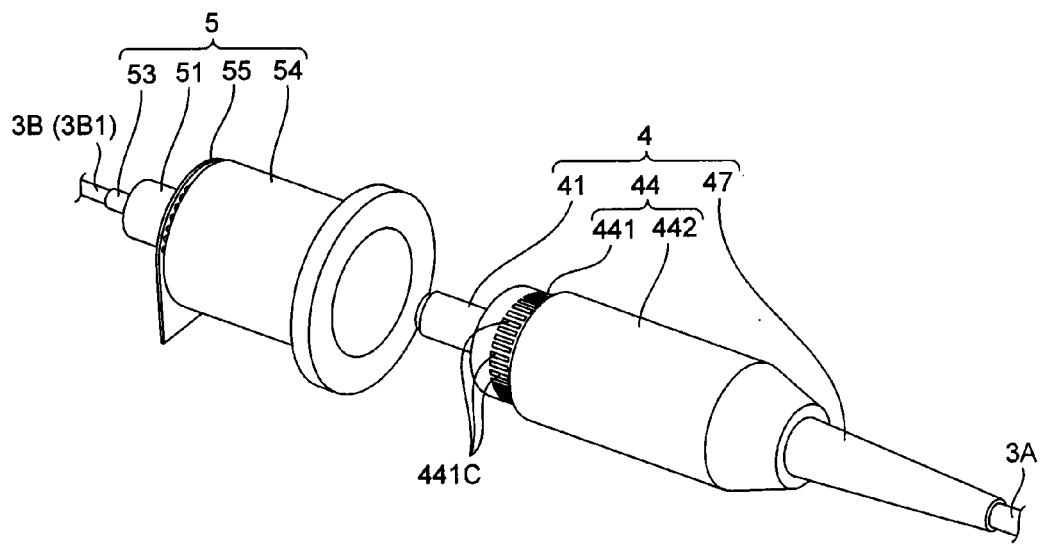
FIG. 2 is an exploded perspective view illustrating the plug and the receptacle illustrated in FIG. 1 viewed from the base end side of the plug.
Figure 3:
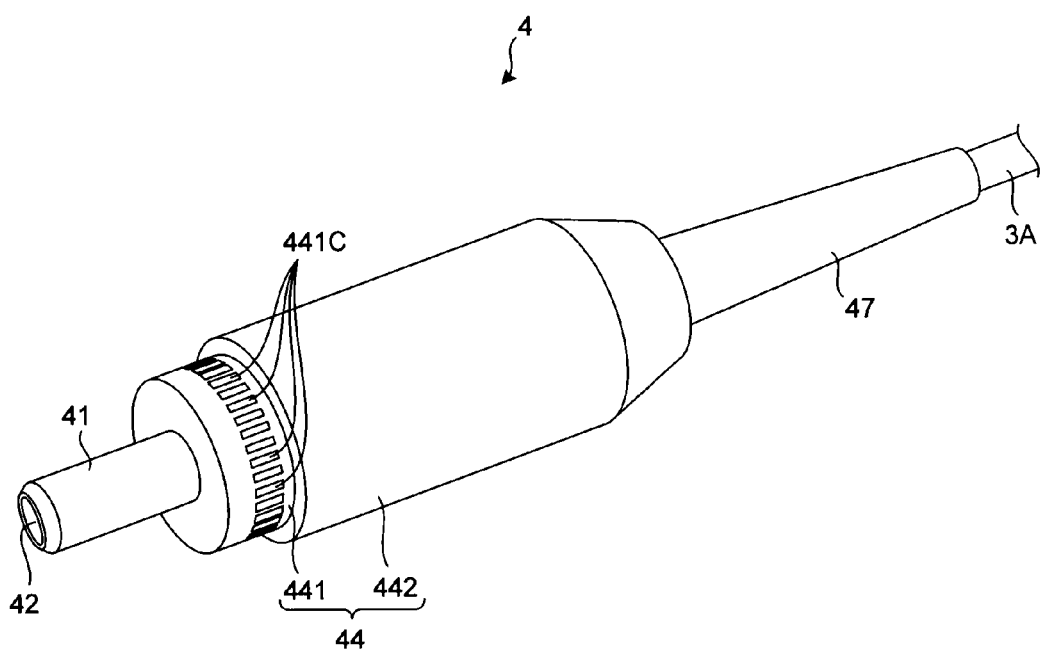
FIG. 3 is a perspective view of the plug illustrated in FIG. 2 viewed from the tip end side thereof.

FIG. 2 is an exploded perspective view illustrating the plug 4 and the receptacle 5 viewed from the base end side of the plug 4 (the side of the camera head 24). FIG. 3 is a perspective view illustrating the plug 4 viewed from the tip end side of the plug 4 (the side to be coupled to the receptacle 5). FIG. 4 is a cross-sectional view of the plug 4 and the receptacle 5 taken along the plane going through the center axis in the coupling direction of the plug 4 and the receptacle 5.

The following describes the configuration of the plug 4 and the configuration of the receptacle 5 in this order with reference to FIGS. 2 through 4.

Configuration of the Plug

The plug 4 includes, a plug-side first outer case 41, a plug-side cover plate (cover member) 42 (FIGS. 3 and 4), a plug-side collimator 43 (FIG. 4), a plug-side second outer case 44, a connecting unit 45 (FIG. 4), a plug-side printed board 46 (FIG. 4), and an elastic member 47.

The plug-side first outer case (the first outer case) 41 has a substantially cylindrical shape as illustrated in FIGS. 2 through 4. The plug-side first outer case 41 may have a tubular shape other than a cylindrical shape such as an ellipse, a square, a rectangle, and a polygon. In the plug-side first outer case 41, the optical fiber 3A1 included in the first transmission cable 3A is inserted through along the central axis of the plug-side first outer case 41. The plug-side first outer case 41 covers the emitting end of an optical signal through the optical fiber 3A1.

Figure 5:
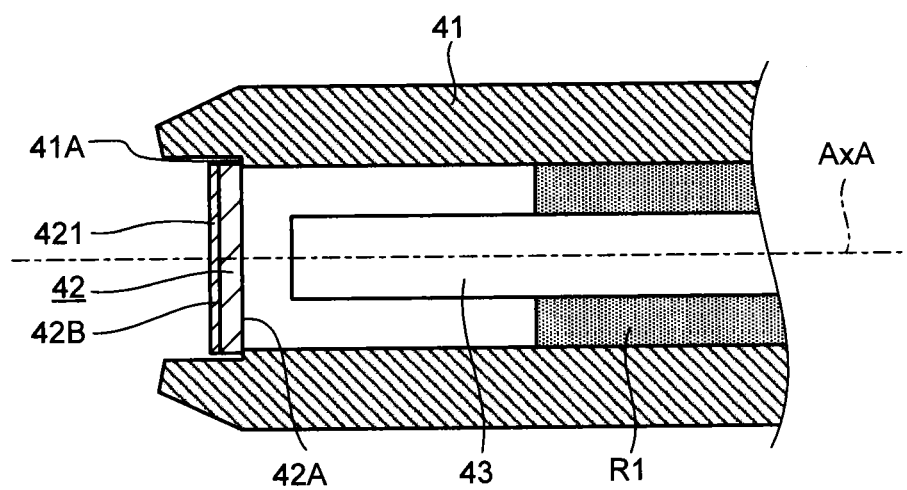
FIG. 5 is an enlarged view of the tip end portion of the plug-side first outer case illustrated in FIG. 4.

FIG. 5 is an enlarged view of the tip end portion of the plug-side first outer case 41 illustrated in FIG. 4.

Around the inner circumferential edge on the tip end of the plug-side first outer case 41, as illustrated in FIG. 5, a mounting member 41A is provided for mounting the plug-side cover plate 42.

Specifically, the mounting member 41A is a recess dented in the direction parallel to the central axis (an optical axis) A×A of the optical fiber 3A1 inserted through the plug 4. The bottom portion of the mounting member 41A is formed flatly. The normal direction of the bottom portion is parallel to the direction of the central axis A×A.

The plug-side cover plate (a cover plate) 42 is provided flatly similar to the mounting member 41A. The plug-side cover plate 42 includes a plate body having first and second plate surfaces 42A and 42B (FIG. 5) provided in parallel with each other.

The plug-side cover plate 42 is attached to the bottom portion of the mounting member 41A and airtightly connected to the plug-side first outer case 41 (the mounting member 41A) by soldering, brazing, bonding, or glass-sealing. Through such a connection, the first plate surface 42A faces the emitting end of an optical signal through the optical fiber 3A1 and faces the inside of the plug-side first outer case 41. On the plug-side cover plate 42, the first and second plate surfaces 42A and 42B intersect at right angles with the central axis A×A. As described above, sealing the tip end side of the plug-side first outer case 41 with the plug-side cover plate 42 prevents a liquid or a foreign material from entering the plug-side first outer case 41, thereby ensuring the reliability of optical communication.

The plug-side cover plate 42 is disposed at a position retracted from the tip end side of the plug-side first outer case 41 toward the base end side of the plug-side first outer case 41 (at a position secluded from the tip end side of the plug-side first outer case 41). This configuration prevents the plug-side cover plate 42 from being touched by hand, thereby preventing a foreign material from sticking to the plug-side cover plate 42. This effect ensures optical communication and prevents reduction of the reliability thereof due to foreign material.

The plug-side cover plate 42 is made of a material permeable to light having the wavelength used for optical transmission. Examples of such a material include glass, sapphire, germanium (Ge), silicon (Si), calcium fluoride ($CaF_2$), and zinc selenide (ZnSe).

If a near-infrared ray with a wavelength of about 850 nm is used for transmitting image data, the plug-side cover plate 42 is made of a material highly permeable to near-infrared radiation. Examples of such a material include glass with a transmittance of equal to or larger than 80% for light ranging from visible ray to a light with a wavelength of about 3 μm, such as quartz glass and various types of optical glasses; sapphire with a transmittance of equal to or larger than 80% for light with a wavelength ranging from about 0.25 to 4 μm; calcium fluoride ($CaF_2$) with a transmittance of equal to or larger than 90% for light with a wavelength ranging from about 0.2 to 8 μm; and zinc selenide (ZnSe) with a transmittance of equal to or larger than 60% for light with a wavelength ranging from about 0.6 to 15 μm.

If an infrared ray with a wavelength of equal to or larger than 2 μm is used for transmitting image data, the plug-side cover plate 42 is made of a material highly permeable to infrared radiation. Examples of such a material include germanium (Ge) with a transmittance of equal to or larger than 40% for light with a wavelength ranging from about 2 to 20 μm; silicon (Si) with a transmittance of equal to or larger than 40% for light with a wavelength ranging from about 1.2 to 6 μm; and chalcogenide glass with a transmittance of equal to or larger than 60% for light with a wavelength ranging from about 2 to 20 μm (controllable depending on the composition of glass).

Out of the above-described materials, the various types of glasses have no anisotropy which a crystal has. This characteristic facilitates application of various types of molding methods and processing methods, enabling to process the material in any desired shape or in any desired thickness. The glasses are thus more preferably used. In addition, the glasses have wider range of their respective compositions to be selected for improving the chemical or thermal resistance, and adjusting easiness of coating. The glasses are thus also preferably used in this respect.

On the second plate surface 42B of the plug-side cover plate 42, a coating film 421 is provided that is resistant to an autoclave. The coating film 421 is made of a material highly permeable to light used for transmitting image data. The coating film 421 having a single layer satisfies the phase condition of antireflection when transmitting image data using light with a single wavelength. However, the coating film 421 having a plurality of layers is preferably used to satisfy the phase condition of antireflection when transmitting image data using light with a plurality of wavelengths.

If a near-infrared ray with a wavelength of about 850 nm having a single layer is used for transmitting image data, the coating film 421 is made of a material highly permeable to infrared radiation, amorphous carbon, for example, that is highly permeable to a near-infrared ray with a wavelength of about 850 nm, in particular. The amorphous carbon has neither crystal structure nor anisotropy, thereby forming an isotropic and dense film. With this configuration, the plug-side cover plate 42 hardly suffers an attack by a drug, thus having resistance to an autoclave. Examples of such amorphous carbon include a hard carbon film (also called a diamond-like carbon (DLC)).

The coating film 421 more preferably has an antireflection function of light for transmitting image data. The plug-side cover plate 42 is made of sapphire, for example. The refractive index of sapphire in the near-infrared region is about 1.766, and the surface reflectivity per plane thereof is 7.7%. On the plug-side cover plate 42 made of sapphire, therefore, 7.7% of the light reflects on the first plate surface 42A and the second plate surface 42B, respectively, allowing only 85% of the light to transmit through the plug-side cover plate 42 totally, which is a substantial transmission loss. To cope with this, the coating film 421 more preferably has an antireflection function of light for transmitting image data to improve the transmittance of the plug-side cover plate 42.

The phase condition of antireflection is publicly known and represented by the formula: $d=\frac{1}{4}(\lambda n)$, where the thickness of the coating film 421 is d, the wavelength of light for transmitting image data is $\lambda$, and the refractive index of the coating film 421 is n. If light with a wavelength of $\lambda=950$ nm is used for transmitting image data, and a hard carbon film with a refractive index n=2.00 is applied to the coating film 421 and if the thickness d of the hard carbon film is about 106 nm, the phase condition is met.

The plug-side collimator 43 is, as illustrated in FIG. 4, disposed in the plug-side first outer case 41 while being connected to the emitting end of the optical fiber 3A1. That is, the plug-side collimator 43 is disposed between the plug-side cover plate 42 and the emitting end of the optical fiber 3A1. The plug-side collimator 43 collimates the light emitted from the emitting end of the optical fiber 3A1 (an optical signal).

Providing the plug-side collimator 43 facilitates manufacturing the plug 4 because the configuration with the plug-side collimator 43 requires not so high accuracy on the mechanical connection to the receptacle 5 in comparison with the configuration without the plug-side collimator 43.

In the above-described plug-side first outer case 41, the base end side of the plug-side first outer case 41 (the periphery of a portion of the plug-side collimator 43, the periphery of the emitting end side of the optical fiber 3A1) is sealed, as illustrated in FIG. 4 or 5, with a sticky sealing material R1 made of silicone resin or epoxy resin, for example. The description on the sealing is provided merely for exemplary purpose and not limiting. For another example, glass sealing may be adopted.

The plug-side second outer case 44 includes an tip-end-side outer case 441 and an base-end-side outer case 442 and has a substantially cylindrical shape as illustrated in FIGS. 2 through 4. The plug-side second outer case 44 may have a tubular shape with any cross section such as an ellipse, a square, a rectangle, a polygon and the like, the tubular shape including a cylindrical shape having a circular cross section.

The tip-end-side outer case 441 includes a cylindrical large outside diameter 441A and a small outside diameter 441B and has a substantially cylindrical shape. The large outside diameter 441A is integrally and coaxially provided with the small outside diameter 441B. The small outside diameter 441B has an outer diameter smaller than that of the large outside diameter 441A and an inner diameter equal to that of the large outside diameter 441A. A base end portion of the plug-side first outer case 41 is fitted into the tip-end-side outer case 441 so that its tip end portion protrudes.

The space between the tip-end-side outer case 441 and the plug-side first outer case 41 is sealed up with an O-ring or a sticky sealing material made of silicone resin or epoxy resin, for example.

On the tip-end-side outer case 441, a plurality of plug-side electrical contacts 4410 are provided that is made of an electrically conductive material.

The plug-side electrical contacts 441C have its one end, as illustrated in FIG. 4, exposed to the outer circumferential surface of the large outside diameter 441A and the other end protruding from the end surface of the base end side. The plug-side electrical contacts 441C extend from the outer circumferential surface of the large outside diameter 441A to the end surface of the base end side of the small outside diameter 441B. Each of the plug-side electrical contacts 441C is disposed with a certain space interposed between itself and the adjacent contact in the circumferential direction of the tip-end-side outer case 441.

The base-end-side outer case 442 is disposed on the base end side relative to the tip-end-side outer case 441 and has a substantially cylindrical shape. The tip end portion of the base-end-side outer case 442 is fitted into the small outside diameter 441B with the first transmission cable 3A being inserted through the base-end-side outer case 442.

The space between the base-end-side outer case 442 and the small outside diameter 441B is sealed with an O-ring or a sticky sealing material made of silicone resin or epoxy resin, for example.

The connecting unit 45 is disposed, as illustrated in FIG. 4, in the base-end-side outer case 442 and electrically couples the plug-side electrical contacts 441C to the plug-side printed board 46. The connecting unit 45 includes a platelike insulator 451 and a plurality of contacts (not illustrated). The insulator 451 has a hole 451A through which the optical fiber 3A1 is inserted. The contacts are made of an electrically conductive material and penetrates the insulator 451 from the front side to the back side. The connecting unit 45 is disposed in the base-end-side outer case 442 so that the insulator 451 intersects at right angles with the central axis A×A. The contacts are electrically coupled to the plug-side electrical contacts 441C protruding from the base end side of the small outside diameter 441B. The contacts are also electrically coupled to the plug-side printed board 46 through an electric wiring 48.

The plug-side printed board 46 is disposed, as illustrated in FIG. 4, along the plane including the central axis A×A and electrically couples the plug-side electrical contacts 4410 to a plurality of electric signal cables 3A2 included in the first transmission cable 3A through the connecting unit 45.

In the above-described base-end-side outer case 442, the base end side of the base-end-side outer case 442 (the periphery of a portion of the first transmission cable 3A, the periphery of the plug-side printed board 46) is sealed, as illustrated in FIG. 4, with a sticky sealing material R2 made of silicone resin or epoxy resin, for example. The description on the sealing is provided merely for exemplary purpose and not limiting. For another example, glass sealing may be adopted.

The elastic member 47 is a member for preventing the first transmission cable 3A from being bent at the inner circumferential edge of the base end portion in the base-end-side outer case 442. The elastic member 47 is made of an elastic material such as rubber and has a substantially cylindrical shape. The tip end portion of the elastic member 47 is fitted into the base end portion of the base-end-side outer case 442 with the first transmission cable 3A being inserted through the elastic member 47.

The space between the elastic member 47 and the base-end-side outer case 442 is sealed with an O-ring or a sticky sealing material made of silicone resin or epoxy resin, for example.

Configuration of the Receptacle

The receptacle 5 includes, as illustrated in FIG. 2 or 4, a receptacle-side first outer case 51, a receptacle-side cover plate 52 (FIG. 4), a receptacle-side collimator 53, a receptacle-side second outer case 54, and a receptacle-side printed board 55.

The receptacle-side first outer case 51 includes a cylindrical large inside diameter 511 disposed on the tip end side (the side to be coupled to the plug 4) and a cylindrical small inside diameter 512 disposed on the base end side and has a substantially cylindrical shape. The large inside diameter 511 is integrally and coaxially provided with the small inside diameter 512. The small inside diameter 512 has an inner diameter smaller than that of the large inside diameter 511 and an outer diameter equal to that of the large inside diameter 511. The receptacle-side first outer case 51 may have a tubular shape with any cross section such as an ellipse, a square, a rectangle, a polygon and the like, the tubular shape including a cylindrical shape having a circular cross section.

The large inside diameter 511 has an inner diameter slightly larger than the outer diameter of the plug-side first outer case 41. The large inside diameter 511 has a length (in the height direction of the cylinder) slightly larger than the portion protruding from the plug-side second outer case 44 (the tip-end-side outer case 441) in the plug-side first outer case 41.

The receptacle-side cover plate 52 includes a translucent plate body and is attached to the uneven portion between the large inside diameter 511 and the small inside diameter 512. The receptacle-side cover plate 52 is connected to the receptacle-side first outer case 51. That is, the receptacle-side cover plate 52 is disposed so as to intersect at right angles with the central axis A×B (the optical axis) (FIG. 4) of the optical fiber 3B1. The connecting method described above may be the same as that of the plug-side cover plate 42 to the plug-side first outer case 41. Alternatively, another connecting method may be adopted. The receptacle-side cover plate 52 may be made of the same material as the plug-side cover plate 42. Alternatively, other different materials may be adopted that have transmittance allowing optical communication.

The receptacle-side collimator 53 is inserted through, as illustrated in FIG. 4, the small inside diameter 512 while being connected to the incidence end of the optical fiber 3B1. The receptacle-side collimator 53 guides light (the optical signal) emitted from the plug-side collimator 43 to the incidence end of the optical fiber 3B1.

Providing the receptacle-side collimator 53 facilitates manufacturing the receptacle 5 because the configuration with the receptacle-side collimator 53 requires not so high accuracy on the mechanical connection to the plug 4 in comparison with the configuration without the receptacle-side collimator 53.

The receptacle-side second outer case 54 has an inner diameter slightly larger than the outer diameter of the plug-side second outer case 44 (the base-end-side outer case 442) and has a substantially cylindrical shape. The receptacle-side first outer case 51 is inserted into the receptacle-side second outer case 54 so that its base end portion protrudes.

The receptacle-side printed board 55 includes a substrate body 551 and a plurality of receptacle-side electrical contacts 552.

The substrate body 551 includes, as illustrated in FIG. 4, a hole 551A penetrating from the front side to the back side on or near the center portion of the substrate body 551. The receptacle-side first outer case 51 is fitted into the hole 551A.

The receptacle-side electrical contacts 552 are made of an electrically conductive material and are electrically coupled to the substrate body 551. The receptacle-side electrical contacts 552 protrude toward inside the receptacle-side second outer case 54. Each of the receptacle-side electrical contacts 552 is disposed with a certain space interposed between itself and the adjacent contact in the circumferential direction of the receptacle-side first outer case 51. The number of receptacle-side electrical contacts 552 is identical to that of the plug-side electrical contacts 441C.

The substrate body 551 electrically couples the receptacle-side electrical contacts 552 to a plurality of electric signal cables 3B2 (FIG. 4) included in the second transmission cable 3B.

While the above-described plug 4 and the receptacle 5 are mechanically coupled to each other, the plug-side first outer case 41 is inserted into the receptacle-side first outer case 51 (the large inside diameter 511). In this state, the central axis A×A of the optical fiber 3A1 coincides with the central axis A×B of the optical fiber 3B1. In addition, the plug-side collimator 43 (the emitting end of the optical fiber 3A1) and the receptacle-side collimator 53 (the incidence end of the optical fiber 3B1) face each other. That is, in this state, the optical signal (the imaging signal) output from the camera head 24 and transmitted through the first transmission cable 3A (the optical fiber 3A1) is ready to be transmitted to the second transmission cable 3B (the control device 7) through the plug 4 and the receptacle 5 (a state capable of optical communications).

While the above-described plug 4 and the receptacle 5 are mechanically coupled to each other, the plug-side second outer case 44 is inserted into the receptacle-side second outer case 54, and the plug-side electrical contacts 441C are coupled to the receptacle-side electrical contacts 552, respectively. That is, in this state, a control signal or the like output from the control device 7 and transmitted through the second transmission cable 3B (a plurality of electric signal cables 3B2) is ready to be transmitted to the first transmission cable 3A (the camera head 24) through the plug 4 and the receptacle 5.

Forming Method of a Hard Carbon Film

The following describes an example of a forming method of a hard carbon film on the plug-side cover plate 42. In the example below, the plug-side cover plate 42 serving as a processed material is made of silicon.

Firstly, the processed material is disposed at a certain position in a processing chamber, which is then vacuated using an oil diffusion pump. After adjusting the pressure in the processing chamber to about $10^{-3}$ Pa, argon gas is introduced from a hollow cathode discharge gun (an HCD gun) made of tantalum to adjust the pressure to 20 Pa.

After that, a voltage of 50 V and a high frequency voltage are applied in a superimposed manner between the HCD gun and the hearth to generate glow discharge plasma in argon gas.

Subsequently, a current of about 100 A is supplied to a coil provided around the hearth to gather the plasma in argon gas. A voltage of 350 V is then applied between an auxiliary electrode (provided to the HCD gun) and the HCD gun, thereby facilitating the discharge between the HCD gun and the hearth.

After the arc discharge between the HCD gun and the hearth ignites, the processing chamber is degassed using the oil diffusion pump without changing the flow rate of argon gas until the pressure in the processing chamber becomes about 0.1 Pa.

After that, at a first stage, the plug-side cover plate 42 is cleaned under the condition "an HCD gun current of 100 A, an argon gas flow rate of 50 sccm, a coil current of 180 A, and a voltage between the processed material and grounding of 800 V" for five minutes.

At a subsequent second stage, a hard carbon film is deposited on the plug-side cover plate 42. Within about one minute after the process is proceeded from the first stage to the second stage, the cleaning condition at the first stage is changed to "an HCD gun current of 150 A, an argon gas flow rate of 10 sccm, a coil current of 200 A, and no voltage to the processed material". Performing the process at the second stage for about 15 minutes generates a hard carbon film of about 0.1 µm thick.

The above-described forming method of a hard carbon film is provided merely for exemplary purpose and not limiting. The hard carbon film can be formed under different conditions depending on the property of a hard carbon film, the film thickness, and the type of the plug-side cover plate 42.

The forming method of a hard carbon film may be a plasma chemical vapor deposition (CVD) method or a physical vapor deposition (PVD) method.

In the plasma CVD method, hydrocarbon gas such as acetylene is used as a material. The material gas is changed to plasma in a chamber, and then the hydrocarbon subject to vapor phase composition is deposited on a surface of a specimen. The hard carbon film generated always contains hydrogen because the material contains hydrogen. Such a plasma CVD method has advantageous effects such as relative low processing temperature (ambient temperature to 200° C.), easiness of forming uniformly in a complicated shape through disposition of an electrode, and a relative short processing time.

In the PVD method, graphite serving as a material is exposed to an ion beam, arc discharge, and glow discharge in a vacuum, the dispersed carbon atoms are deposited on a surface of a specimen of a target object. In the PVD method, a metal-added hard carbon film or a hard carbon film containing only carbon can also be formed.

Any one of the above-described forming methods of a hard carbon film can be selected as appropriate depending on the required property of the coating film 421.

The embodiment of the present invention can provide an optical connector and a medical device that have resistance to an autoclave and are suitable for transmitting an optical signal by providing a coating film 421 made of amorphous carbon on a surface on the tip end side of the plug-side cover plate 42 sealing the tip end side of the plug-side first outer case 41 coupled to the receptacle 5.

The embodiment of the present invention can achieve optical transmission with a simple configuration if an optical signal with a single wavelength is transmitted with high transmittance, by providing the coating film 421 having a single layer.

According to the present embodiment, the plug-side cover plate 42 is disposed at a position retracted from the tip end side of the plug-side first outer case 41 toward the base end side of the plug-side first outer case 41 (at a position secluded inside the plug-side first outer case 41).

This configuration prevents a user from directly touching the plug-side cover plate 42 by hand, thereby preventing a foreign material from sticking to the plug-side cover plate 42. This effect ensures optical communication and prevents reduction of the reliability thereof due to foreign material.

Modifications

Figure 6:
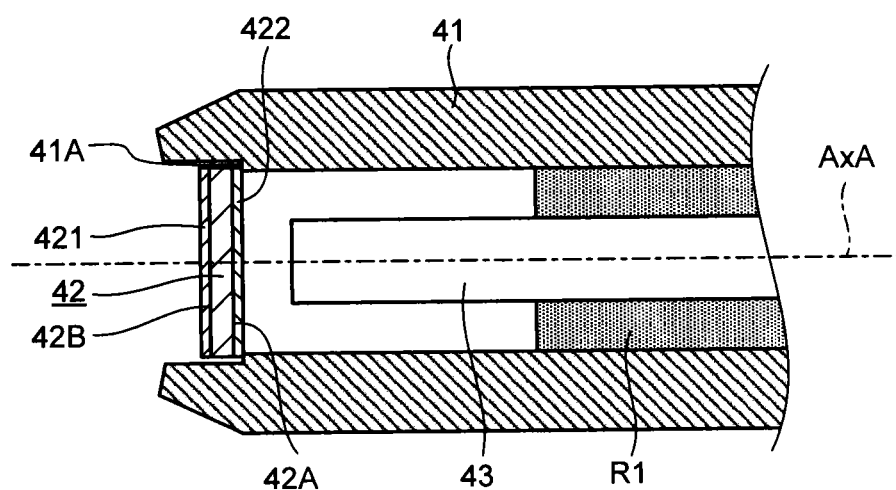
FIG. 6 is an enlarged view of the tip end portion of the plug-side first outer case according to a first modification of the embodiment of the present invention.

FIG. 6 is an enlarged view of the tip end portion of the plug-side first outer case 41 according to a first modification of the present embodiment. In the first modification, a coating film (a second coating film) 422 is provided on the first plate surface 42A of the plug-side cover plate 42. The coating film 422 is made of a material having the same permeability as that of the coating film 421. The coating film 421 may be made of a material different from that of the coating film 422.

In the first modification, the coating film is provided on both surfaces of the plug-side cover plate 42, allowing use of the plug-side cover plate 42 regardless of its front and back surfaces, thereby increasing the productivity of the optical connector. The coating films 421 and 422 each having a single layer satisfy the phase condition of antireflection when transmitting image data using light with a single wavelength. However, the coating films 421 and 422 each having a plurality of layers are preferably used to satisfy the phase condition of antireflection when transmitting image data using light with a plurality of wavelengths.

The coating film 422 more preferably has an antireflection function of light. That is, the coating film 422 has a film thickness satisfying the phase condition of antireflection in the same manner as the thickness of the film of the coating film 421.

Figure 7:
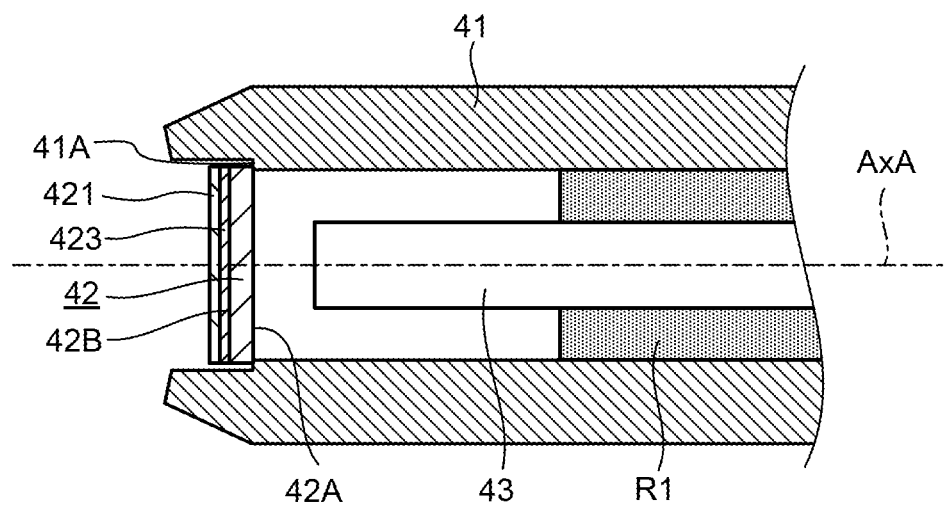
FIG. 7 is an enlarged view of the tip end portion of the plug-side first outer case according to a second modification of the embodiment of the present invention.

FIG. 7 is an enlarged view of the tip end portion of the plug-side first outer case 41 according to a second modification of the present embodiment. In the second modification, an antireflection film 423 is disposed on the second plate surface 42B of the plug-side cover plate 42, and a coating film 421 is disposed on a surface on the tip end side of the antireflection film 423. The antireflection film 423 is formed through typical antireflective coating (AR coating). The antireflection film 423 is made of magnesium fluoride ($MgF_2$) or silica ($SiO_2$), for example.

In the second modification, the antireflection film 423 is provided on a surface of the second plate surface 42B, reducing reflection on the surface of the plug-side cover plate 42, thereby enabling efficient optical transmission. In the second modification, a coating film 421 is provided on a surface of the tip end side of the antireflection film 423 provided to the second plate surface 42B, thereby preventing the plug cover plate 42 and the antireflection film 423 from being influenced by the autoclave.

In the second modification, the coating film 422 may be provided on the first plate surface 42A in the same manner as the first modification.

Figure 8:
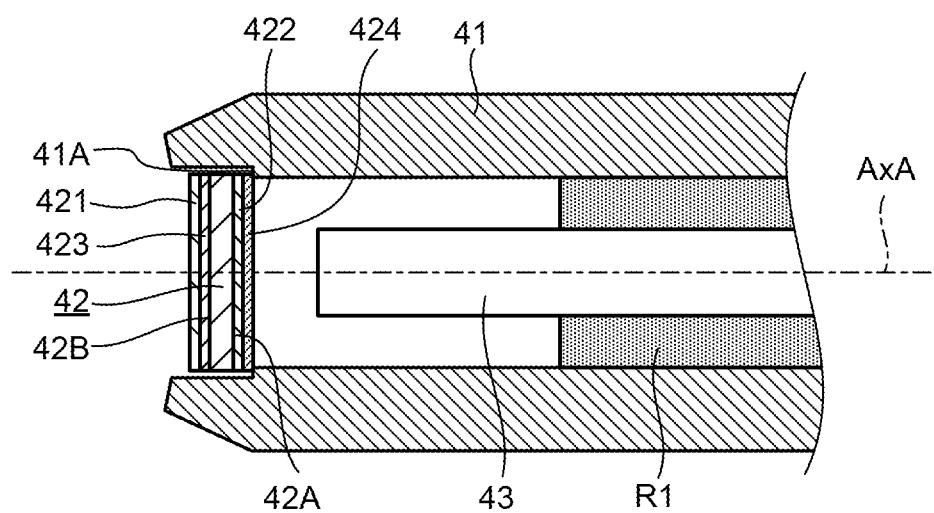
FIG. 8 is an enlarged view of the tip end portion of the plug-side first outer case according to a third modification of the embodiment of the present invention.

FIG. 8 is an enlarged view of the tip end portion of the plug-side first outer case 41 according to a third modification of the present embodiment. In the third modification, a coating film 422 is disposed on the first plate surface 42A of the plug-side cover plate 42, and an antireflection film (a second antireflection film) 424 is disposed on a surface on the coating film 422 that faces the tip end side of the plug-side collimator 43. In addition, an antireflection film 423 is disposed on the second plate surface 42B of the plug-side cover plate 42, and a coating film 421 is disposed on a surface on the tip end side of the antireflection film 423. The antireflection film 424 is made of the same material as the antireflection film 423.

In the third modification, the antireflection films 423 and 424 are provided on both surfaces of the plug-side cover plate 42, respectively, thereby further reducing reflection on the surfaces of the plug-side cover plate 42. On the first plate surface 42A, the coating film 422 having a relative large refractive index is provided on the surface of the plug-side cover plate 42 having a relative small refractive index, which is a preferable configuration from an optical aspect. Furthermore, the plug 4 is sealed, thereby preventing the antireflection film 423 from being influenced by temperature or a reagent.

Figure 9:
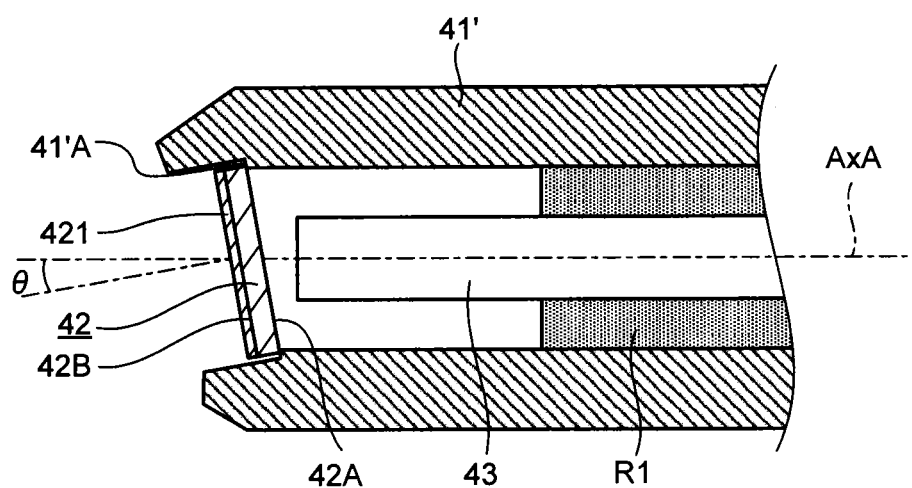
FIG. 9 is an enlarged view of the tip end portion of the plug-side first outer case according to a fourth modification of the embodiment of the present invention.

FIG. 9 is an enlarged view of the tip end portion of the plug-side first outer case 41' according to a fourth modification of the present embodiment. In the fourth modification, a coating film 421 is provided on the second plate surface 42B of the plug-side cover plate 42. The normal direction of the second plate surface 42B of the plug-side cover plate 42 inclines by an angle of θ relative to the central axis (the optical axis) A×A of the optical fiber 3A1 inserted into the plug 4.

Around the inner circumferential edge on the tip end of the plug-side first outer case 41', as illustrated in FIG. 9, a mounting member 41'A is provided for mounting the plug-side cover plate 42. The mounting member 41'A is a recess dented in the direction inclined by an angle of θ relative to the central axis (the optical axis) A×A of the optical fiber 3A1 inserted into the plug 4. The bottom portion of the mounting member 41'A is formed flatly. The normal direction of bottom portion inclines by an angle of θ relative to the central axis A×A.

The angle θ is preferably defined from one degree or larger to 45 degrees or smaller, and more preferably from five degrees or larger to 20 degrees or smaller. Any angle θ inclined by equal to or larger than one degree provides an advantageous effect of reducing the reflected light to the plug-side collimator 43. The angle θ inclined by an angle larger than 45 degrees requires a wider area of the plug-side cover plate 42 to achieve optical transmission, which in turn requires higher accuracy of finishing and assembling in addition to upsizing of the plug-side cover plate 42, in comparison with the angle θ gently inclined. This is the reason why the angle θ is preferably defined equal to 45 degrees or smaller. The most preferred balanced angle θ is ranged from five degrees or larger to 20 degrees or smaller because the angle best balances some conditions such as reflected light to the plug-side collimator 43, the size of a window member, and accuracy of finishing and assembling.

In the fourth modification, if a portion of light emitted from the plug-side collimator 43 is reflected on the plug-side cover plate 42, the reflected light advances in such a direction avoiding the plug-side collimator 43. This configuration generates no reversed light from the reflected light, thereby sufficiently ensuring the reliability of optical communication.

Other Embodiments

While certain embodiments according to the present invention have been described, these embodiments have been presented by way of example only, and are not intended to limit the scope of the invention.

In the above-described embodiments, the optical connector according to the present invention includes the plug 4 serving as a male connector and the counter-connector includes the receptacle 5 serving as a female connector. The description is provided merely for exemplary purpose and not limiting. For another example, the optical connector according to the present invention may include a receptacle and the counter-connector may include a plug.

In the above-described embodiments, the plug-side cover plate 42 includes the first plate surface 42A provided flatly, however, the first plate surface 42A may be provided curvedly. Also in this example in which the first plate surface is provided curvedly, the light emitted from the plug-side collimator 43 and reflected on the first plate surface preferably advance in such a direction avoiding the plug-side collimator 43.

In the above-described embodiments, optical communication is achieved through one channel (channel of communications); however, a plurality of channels may be used. In this example in which a plurality of channels are used for achieving optical communication, the cover plate may be provided for each channel. Alternatively, a smaller number of cover plates than the number of channels may be provided, by collecting the channels into a smaller number of groups.

In the above-described embodiments, the optical connector is used for the endoscope apparatus 1. The description is provided merely for exemplary purpose and not limiting. The optical connector may be used for other medical devices that transmit optical signals. For another example, the optical connector according to the embodiment invention may be used in the industrial field to be applied to other endoscope apparatuses or other electronic devices for observing the inside of an observation object such as mechanical structures.

An optical connector and a medical device have resistance to an autoclave and are suitable for transmitting an optical signal by providing a coating film made of amorphous carbon on a surface on the tip end side of a cover plate sealing the tip end side coupled to a counter-connector in a first outer case.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An optical connector for coupling to a counter-connector mechanically and optically, a portion of an optical transmission line transmitting an optical signal being disposed in the optical connector, the optical connector comprising:
    a first outer case through which the optical transmission line is inserted and that covers an incidence end or an emitting end of an optical signal through the optical transmission line;
    a cover plate that is permeable to an optical signal and air tightly seals a tip end side of the first outer case, the tip end side being coupleable to the counter-connector; and
    a coating film made of amorphous carbon that is disposed on a surface on the tip end side of the cover plate.

2. The optical connector according to claim 1, wherein the coating film has a single layer.

3. The optical connector according to claim 1, wherein a film thickness of the coating film satisfies a phase condition of antireflection in respect of a refractive index of the cover plate and a wavelength of the optical signal.

4. The optical connector according to claim 1, further comprising a antireflection film that is disposed between the cover plate and the coating film and that prevents reflection of the optical signal on the cover plate.

5. The optical connector according to claim 1, further comprising a second coating film made of the amorphous carbon that is disposed on a surface on a base end side of the cover plate.

6. The optical connector according to claim 5, wherein the second coating film has a single layer.

7. The optical connector according to claim 5, wherein a film thickness of the second coating film satisfies a phase condition of antireflection in respect of a refractive index of the cover plate and a wavelength of the optical signal.

8. The optical connector according to claim 5, further comprising a second antireflection film that is disposed on a surface of the second coating film and that prevents reflection of the optical signal on the cover plate.

9. The optical connector according to claim 1, wherein the cover plate is disposed at a position retracted from the tip end side of the first outer case toward the base end side of the first outer case.

10. The optical connector according to claim 1, wherein the amorphous carbon is a hard carbon film.

11. The optical connector according to claim 1, herein the cover plate is made of a material permeable to infrared radiation.

12. A medical device capturing an image of a subject, the medical device comprising:
   an optical connector for coupling to a counter-connector mechanically and optically, a portion of an optical transmission line transmitting an optical signal being disposed in the optical connector, the optical connector including:
      a first outer case through which the optical transmission line is inserted and that covers an incidence end or an emitting end of an optical signal through the optical transmission line;
      a cover plate that is permeable to an optical signal and air tightly seals a tip end side of the first outer ease, the tip end side being coupleable to the counter-connector; and
      a coating film made of amorphous carbon that is disposed on a surface on the tip end side of the cover plate.

13. The medical device according to claim 12, comprising:
   an endoscope that captures an image of an inside of a subject and outputs an optical signal based on an imaging signal corresponding to the captured image; and
   a control device that inputs the optical signal through a first transmission cable and a second transmission cable and controls an operation of the endoscope, wherein
   the first transmission cable and the second transmission cable are coupled to each other through the optical connector and a counter-connector coupled to the optical connector mechanically and optically.

14. The medical device according to claim 13, wherein the optical connector is coupled to the first transmission cable coupled to the endoscope out of the first transmission cable and the second transmission cable.

* * * * *